United States Patent
Baughman et al.

(10) Patent No.: US 7,806,686 B2
(45) Date of Patent: Oct. 5, 2010

(54) ANCHOR APPARATUS AND METHOD FOR ORTHODONTIC APPLIANCES

(75) Inventors: David Baughman, Louisville, KY (US); Jack Fisher, Memphis, TN (US)

(73) Assignee: Toads LLC, Louisville, KY (US)

( * ) Notice: Subject to any disclaimer, the term of this patent is extended or adjusted under 35 U.S.C. 154(b) by 739 days.

(21) Appl. No.: 11/508,909

(22) Filed: Aug. 24, 2006

(65) Prior Publication Data

US 2008/0050691 A1 Feb. 28, 2008

(51) Int. Cl.
*A61C 7/00* (2006.01)
*A61C 8/00* (2006.01)

(52) U.S. Cl. .......................................... 433/18; 433/174

(58) Field of Classification Search ................... 433/18, 433/24, 172, 173, 174, 175, 176; 606/305, 606/307, 308, 232; 411/372.1, 531
See application file for complete search history.

(56) References Cited

U.S. PATENT DOCUMENTS

| | | | | |
|---|---|---|---|---|
| 951,437 | A * | 3/1910 | Gehrke | 220/304 |
| 2,226,491 | A * | 12/1940 | Gustafson | 411/186 |
| 2,490,364 | A * | 12/1949 | Livingston | 606/68 |
| 2,959,204 | A * | 11/1960 | Rigot | 411/186 |
| 3,469,490 | A * | 9/1969 | Pearce, Jr. | 411/371.1 |
| 4,350,465 | A * | 9/1982 | Lovisek | 411/186 |
| 4,468,200 | A | 8/1984 | Munch | |
| 4,812,095 | A * | 3/1989 | Piacenti et al. | 411/188 |
| 4,988,351 | A * | 1/1991 | Paulos et al. | 606/232 |
| 5,263,996 | A | 11/1993 | Filhol | |
| 5,433,719 | A * | 7/1995 | Pennig | 606/312 |
| 5,453,010 | A | 9/1995 | Klein | |
| 5,507,643 | A | 4/1996 | Klein | |
| 5,522,843 | A * | 6/1996 | Zang | 606/232 |
| 5,564,924 | A | 10/1996 | Kwan | |
| 5,697,779 | A | 12/1997 | Sachdeva et al. | |
| 5,725,345 | A * | 3/1998 | Zhov | 411/369 |
| 5,746,560 | A * | 5/1998 | Barth et al. | 411/188 |
| 5,814,070 | A * | 9/1998 | Borzone et al. | 606/232 |
| 5,871,504 | A | 2/1999 | Eaton et al. | |
| 5,925,047 | A * | 7/1999 | Errico et al. | 606/65 |
| 6,015,410 | A * | 1/2000 | Tormala et al. | 606/232 |
| 6,027,523 | A | 2/2000 | Schmieding | |
| 6,139,565 | A | 10/2000 | Stone et al. | |
| 6,290,499 | B1 | 9/2001 | Lazzara et al. | |

(Continued)

*Primary Examiner*—Cris L Rodriguez
*Assistant Examiner*—Michael R Ballinger
(74) *Attorney, Agent, or Firm*—Frank Presta

(57) ABSTRACT

An apparatus and method for anchoring orthodontic appliances or the like in the mouth wherein anchor screws of different constructions are installed in the bone in different areas of the mouth to insure adequate bone contact and retention. Each of the anchor screws has a threaded portion and a washer portion at the outer end of the threaded portion which is of sufficient width to engage the adjacent exterior bone surface when the threaded portion is installed in the bone to provide lateral support for the threaded portion. In some cases, the threaded portion is provided with threads of different sizes and the washer portion is provided with an exterior thread for cutting through gum tissue to enable the washer portion to engage the underlying adjacent exterior bone surface when the threaded portion is installed in the bone. Each anchor screw is provided with a lateral bore at the outer end thereof for receiving a ligature or the like therethrough to prevent the anchor screw from falling in the mouth.

4 Claims, 12 Drawing Sheets

U.S. PATENT DOCUMENTS

| | | | |
|---|---|---|---|
| 6,312,259 B1 | 11/2001 | Kvarnstrom et al. | |
| 6,575,742 B2 * | 6/2003 | Kyung et al. | 433/18 |
| 6,575,976 B2 * | 6/2003 | Grafton | 606/916 |
| 6,648,892 B2 * | 11/2003 | Martello | 606/319 |
| 6,648,893 B2 * | 11/2003 | Dudasik | 606/327 |
| 6,669,473 B1 * | 12/2003 | Maino | 433/18 |
| 6,689,137 B2 * | 2/2004 | Reed | 606/311 |
| 6,800,078 B2 * | 10/2004 | Reed | 606/308 |
| 6,997,711 B2 | 2/2006 | Miller | |
| 7,101,177 B2 * | 9/2006 | Lin | 433/18 |
| 2002/0182560 A1 * | 12/2002 | Park et al. | 433/18 |
| 2003/0105465 A1 * | 6/2003 | Schmieding et al. | 606/73 |
| 2004/0059336 A1 * | 3/2004 | Lombardo et al. | 606/72 |
| 2004/0157187 A1 * | 8/2004 | Lin | 433/18 |
| 2004/0166460 A1 * | 8/2004 | Devincenzo | 433/18 |
| 2005/0059972 A1 | 3/2005 | Biscup | |
| 2005/0095550 A1 * | 5/2005 | Kim et al. | 433/18 |
| 2005/0100854 A1 * | 5/2005 | Kyung | 433/18 |
| 2005/0130093 A1 * | 6/2005 | Lin | 433/18 |
| 2005/0227197 A1 * | 10/2005 | Lin | 433/18 |
| 2006/0004365 A1 | 1/2006 | Schmieding et al. | |
| 2006/0046229 A1 | 3/2006 | Teich | |
| 2006/0100629 A1 * | 5/2006 | Lee | 606/73 |
| 2006/0199138 A1 * | 9/2006 | Corti et al. | 433/18 |
| 2007/0083206 A1 * | 4/2007 | Du | 606/73 |
| 2007/0122764 A1 * | 5/2007 | Balfour et al. | 433/19 |

* cited by examiner

ANCHOR APPARATUS AND METHOD FOR ORTHODONTIC APPLIANCES

CROSS-REFERENCES TO RELATED APPLICATIONS

N/A

STATEMENT REGARDING FEDERALLY SPONSORED RESEARCH OR DEVELOPMENT

N/A

REFERENCE TO A MICROFICHE APPENDIX

N/A

BACKGROUND OF THE INVENTION

1. Field of the Invention

The present invention relates to a new and improved anchor apparatus and method for orthodontic appliances and, more particularly, to such an anchor apparatus and method wherein different anchor devices are used for different areas of the mouth to ensure adequate lateral and longitudinal support in each area of the mouth.

2. Description of the Background Art

In the current state of the art, self-tapping and standard bone screws of a common construction are used in all areas of the mouth for anchoring orthodontic appliances or the like. These screw constructions are prone to failure or movement owing to the thin cortical bone in some portions of the mouth. Differences in the bone structure and in the covering tissue complicate usage of a common screw construction for all areas of the mouth. For example, there is a need for a thin anchor in the incisal mouth area to avoid root contact and to allow for installation close to a tooth. Also, in the zygomatic process of the maxillary bone, the surrounding tissue often is deeper than the head of the typical bone screw, thereby making it difficult to attach a ligature or other retaining device to the bone screw.

In most cases, interference fit nut drivers are used to prevent the screw from dropping into the mouth. Such nut drivers must often be wiggled from side to side for release with the possibility of unseating the screw during the process. Also, the interference fit is not a 100% reliable solution to preventing the screw from dropping into a patient's mouth with the potential of it being swallowed and requiring hospitalization for removal.

A further disadvantage of existing bone screw constructions are that they have no radial support and thus rely on the support of the screw threads alone in the perpendicular access of installation. Accordingly, such screw constructions are subject to failure or movement when subjected to lateral or radial forces.

There is a need, therefore, for a new and improved anchor apparatus and method for orthodontic appliances which insures that the anchor or bone screws are firmly seated in different areas of the mouth and are not subject to failure or movement when subjected to lateral forces. There is also a need for an anchor apparatus and method that prevents an anchor screw from being unseated during the installation process and dropping into a patient's mouth. The new and improved anchor apparatus and method of the present invention fills this need.

BRIEF SUMMARY OF THE INVENTION

In accordance with the anchor apparatus and method of the present invention, anchor screws of different constructions are used for different areas of the mouth to insure adequate bone contact and retention, and lateral or radial support in each area, as well as the positioning of the screw in each area such that its head portion is adequately exposed outside of the covering tissue to facilitate the connection of a ligature or other device thereto for connecting to an orthodontic device.

In each case, the anchor screw is provided with an enlarged washer portion for engagement with the cortical bone and having a radial width sufficient to provide lateral support for the threaded end portion extending into the bone to prevent its failure or movement when subjected to lateral forces.

Also, in each case, the outer head portion of each anchor screw is provided with a transverse bore and aligned recesses such that a ligature can be passed therethrough and extended through a cannulated driver that serves to rotate and anchor the screw. In this manner, the screw is prevented from separating from the driver because of the ligature passing through the driver that holds the screw in place.

In accordance with the present invention, illustrative examples of the anchor screw constructions for different areas of the mouth are as follows:

1. For the incisal area of the mouth, an anchor screw having one thread size is used and is of a length and diameter to be placed between the roots of the lower anterior teeth.
2. For the palatal mouth area, the anchor screw has two thread sizes such that the initial or inner thread portion penetrates the bone first and an intermediate portion of a larger thread size anchors in the cortical bone. At the inner end of the washer portion, a large diameter threaded portion is provided for cutting through the gingival tissue of the palate such that the inner surface of the washer portion can seat against the bone to provide adequate lateral support.
3. The anchor screw for the zygomatic process of the maxillary bone is provided with a single thread size and has a washer portion of increased longitudinal size or height such that its outer portion extends beyond the gum tissue in this area.
4. The anchor device to be placed mesial to either the upper or lower molars has a construction similar to that of the palatal anchor device except that the longitudinal length or height of the head portion is not as large as that of the palatal anchor screw for the reason that the tissue in these areas is of less thickness than in the palatal area.

In accordance with a further aspect of the present invention, an anchor screw may provided with a flexible and resilient washer adjacent the washer portion thereof such that the washer engages the bone for lateral support even when the screw is inserted at different angles into the bone. The inner head portion of the screw can be provided with inwardly extending annular sharp portions for anchoring into the flexible and resilient washer when the screw is installed in the bone.

DETAILED DESCRIPTION OF THE INVENTION

In accordance with the new and improved anchor apparatus and method of the present invention, anchor screws of different constructions are provided for different areas of the mouth to anchor orthodontic appliances or the like. The anchor screws are constructed to insure adequate bone contact and retention and lateral support in each area of the mouth to prevent movement or failure of the screws when subjected to lateral forces or the like.

Figure 1:
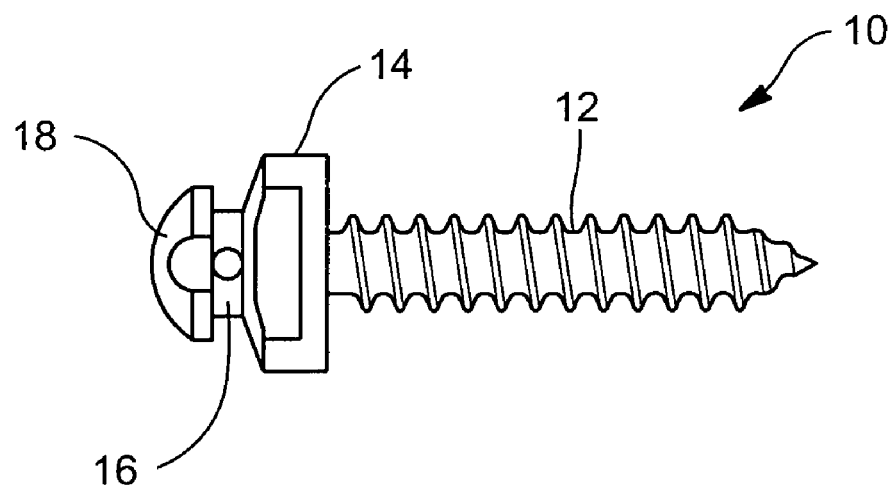
FIG. 1 is a side elevational view of an incisal anchor screw of the present invention.
Figure 2:
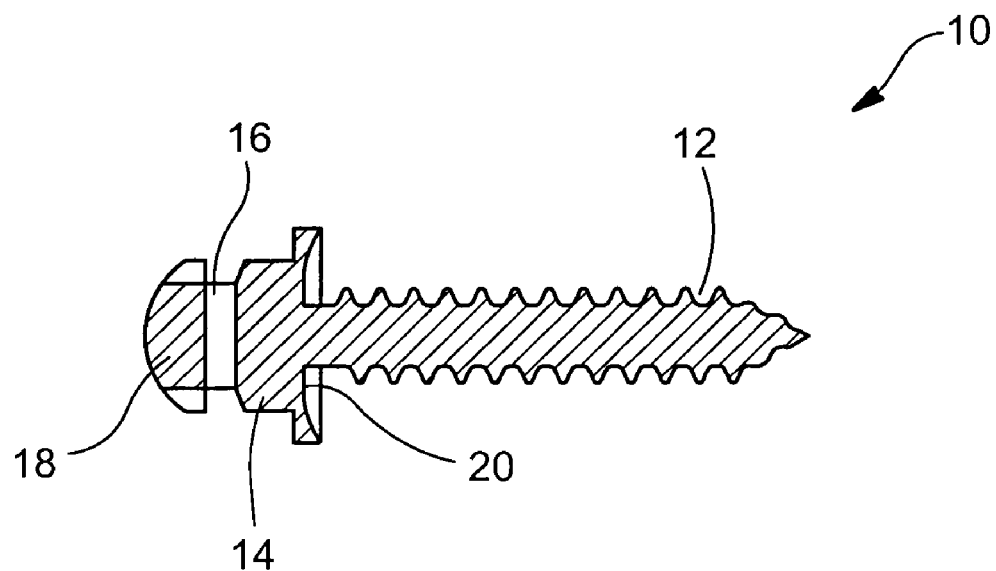
FIG. 2 is a side elevational view in section of the incisal anchor screw as shown in FIG. 1.
Figure 3:
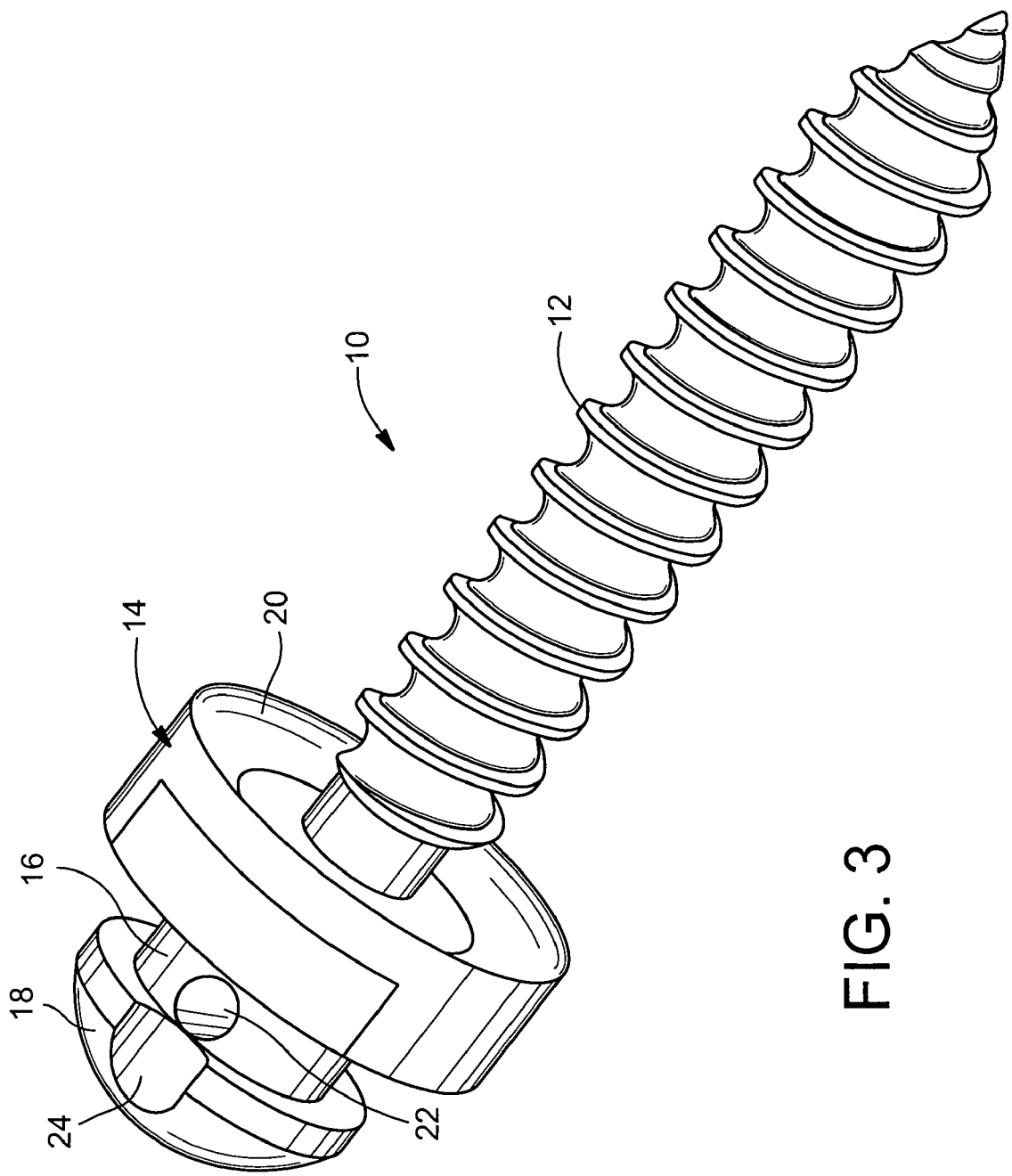
FIG. 3 is a perspective view of the incisal anchor screw shown in FIG. 1.

FIGS. 1-3 illustrate an anchor screw 10 for the incisal area of the mouth. The screw 10 comprises a threaded portion 12 that merges outwardly with an enlarged washer portion 14 that is connected to a narrower neck portion 16 that is in turn connected to a head portion 18 of larger size than the neck portion and of smaller size than the washer portion. The threaded portion 12 is of a size such that it can be placed between the roots of the lower anterior teeth, and the washer portion 14 is of sufficient width or diameter to provide adequate lateral support for the threaded portion 12 when the interior surface of the washer portion 14 engages the adjacent exterior cortical bone surface upon installation of the screw 10. As shown in FIGS. 2 and 3, the inner surface 20 of the washer portion 14 can be concave such that the outer edge portion thereof can cut through the gum tissue and engage the outer bone surface to provide lateral support for the threaded portion 12 when it is fully inserted in the adjacent bone area.

The neck portion 16 is provided with a bore 22 therethrough and the head portion 18 is provided with recesses 24 aligned with the outer ends of the bore 22 such that a ligature (not shown) or the like can be passed through the bore 22 and outwardly through the recesses 24 through a cannulated driver (not shown) or the like for rotating and installing the screw in the desired position in the incisal area. In this manner, the screw 10 is prevented from separating from the driver because of the ligature passing through the driver that holds the screw in place.

As an illustrative example and not by way of limitation, the threaded portion 12 may have a 1.5 mm thread diameter and an 8.0 mm thread length. The washer portion 14 may be approximately 1 mm in thickness or longitudinal length.

Figure 4:
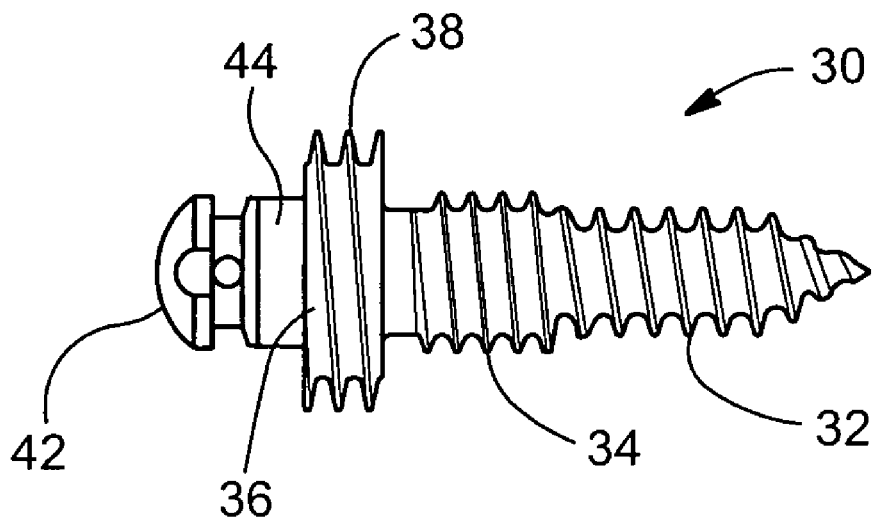
FIG. 4 is a side elevational view of a palatal anchor screw of the present invention.
Figure 5:
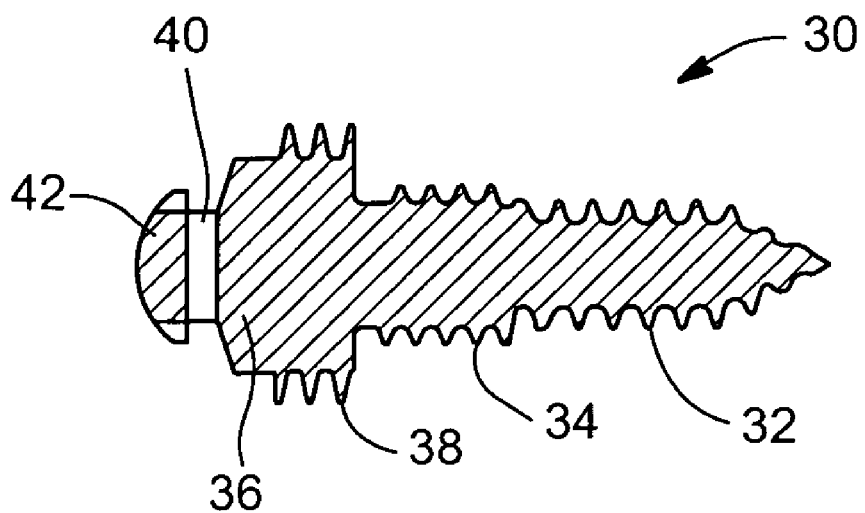
FIG. 5 is a side elevational view in section of the palatal anchor screw as shown in FIG. 4.
Figure 6:
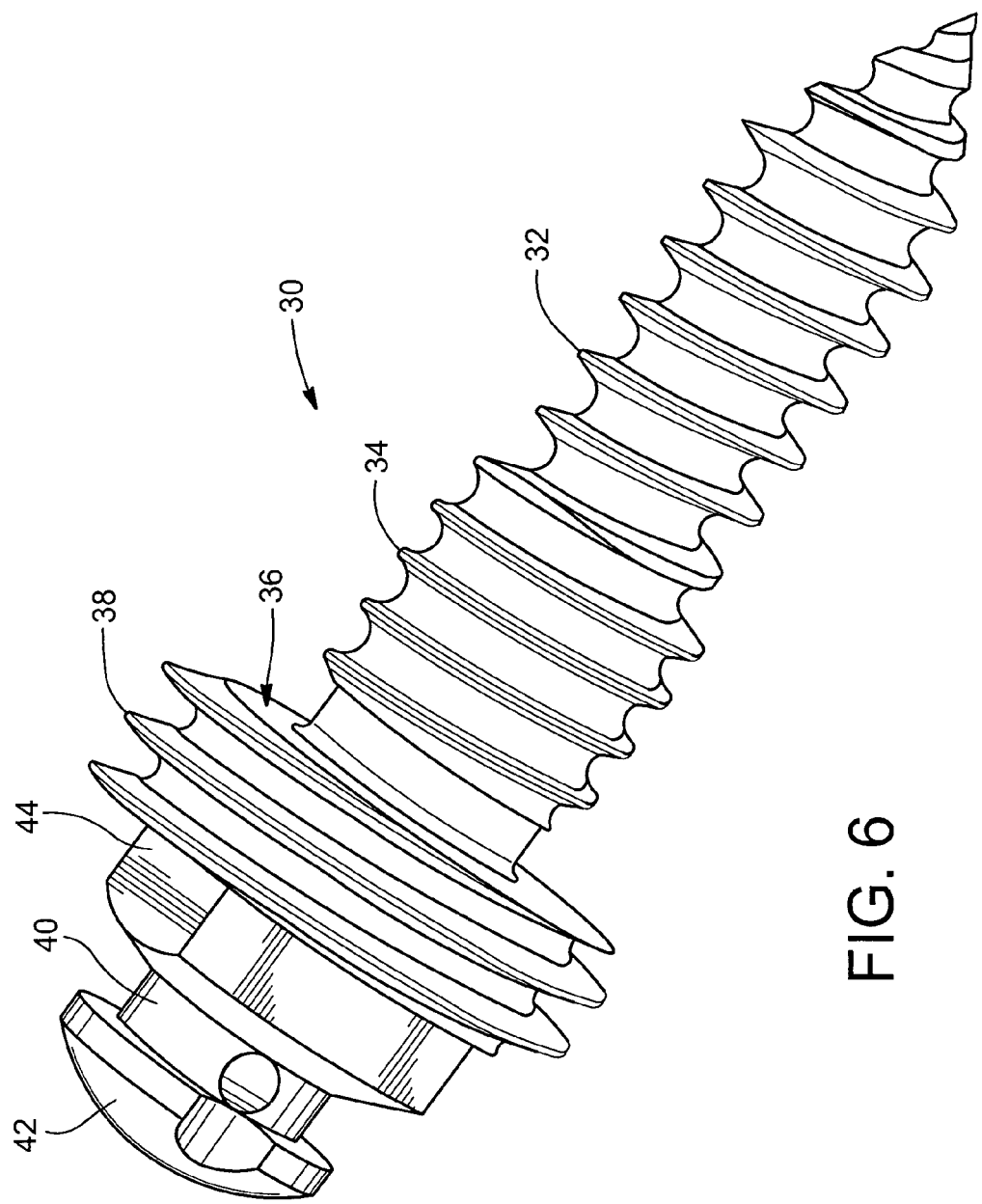
FIG. 6 is a perspective view of the palatal anchor screw shown in FIG. 4.

FIGS. 4, 5 and 6 illustrate an anchor screw 30 for the palatal area of the mouth which comprises an inner threaded portion 32 and an intermediate threaded portion 34 of a size larger than the inner threaded portion 32. The anchor screw 30 has an enlarged washer portion 36 having threads 38 on the exterior surface thereof. The washer portion 36 merges outwardly with a neck portion 40 and a head portion 42 of a construction similar to that of the neck portion 16 and head portion 18 of the incisal anchor screw 10 shown in FIGS. 1-3 and thus are not described in detail herein. The outer end 44 of the washer portion 36 adjacent the neck portion 40 is in the form of an angled nut such that it can be engaged by a cannulated driver (not shown) or the like for rotating and installing the anchor screw 30 in a desired position in the mouth.

In the use of the palatal anchor screw 30, the inner smaller threaded portion 32 penetrates the bone first and the larger intermediate threaded portion 34 then engages the cortical bone to anchor the screw therein. The threads 38 on the washer portion 36 cut through the surrounding gum tissue to facilitate the engagement of the inner surface of the washer portion 36 with the outer surface of the cortical bone to provide adequate lateral support for the threaded portions 32 and 34 installed in the bone.

As an illustrative example and not by way of limitation, the inner portion 32 may have a 2.0 mm starter thread and the intermediate portion 34 may have a 2.5 mm final thread. The thread length may be 6.5 mm. The threaded head portion 36 may have a 4 mm outer diameter and may be 3 mm in thickness.

Figure 7:
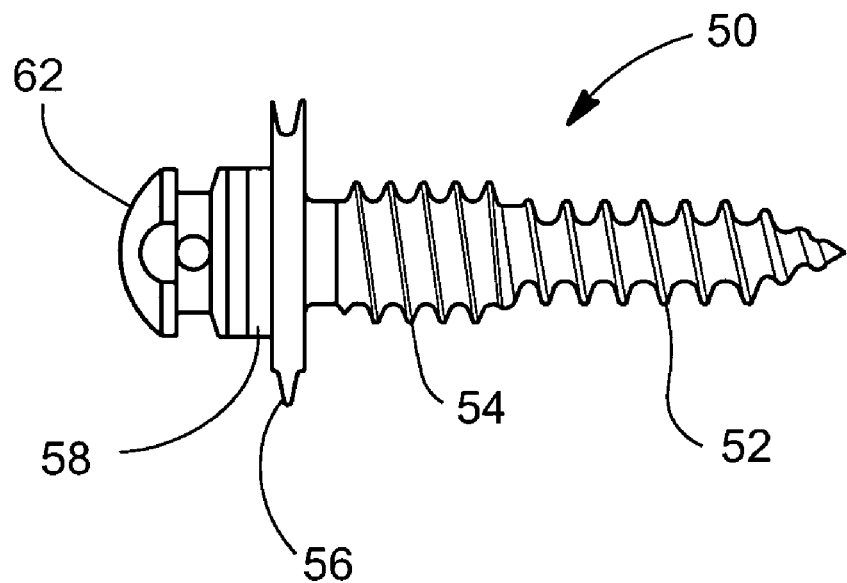
FIG. 7 is a side elevational view of a mesial anchor screw of the present invention.
Figure 8:
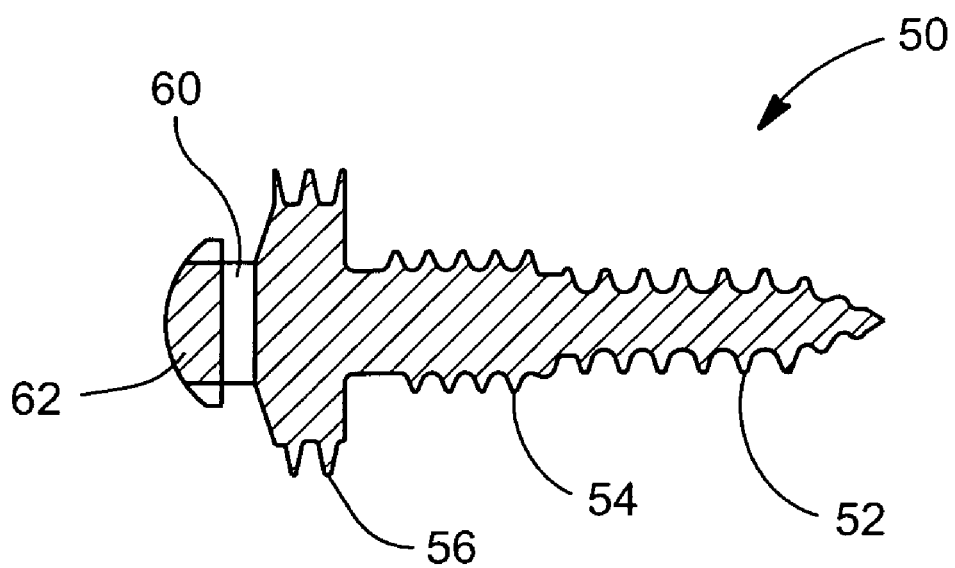
FIG. 8 is a side elevational view in section of the mesial anchor screw as shown in FIG. 7.
Figure 9:
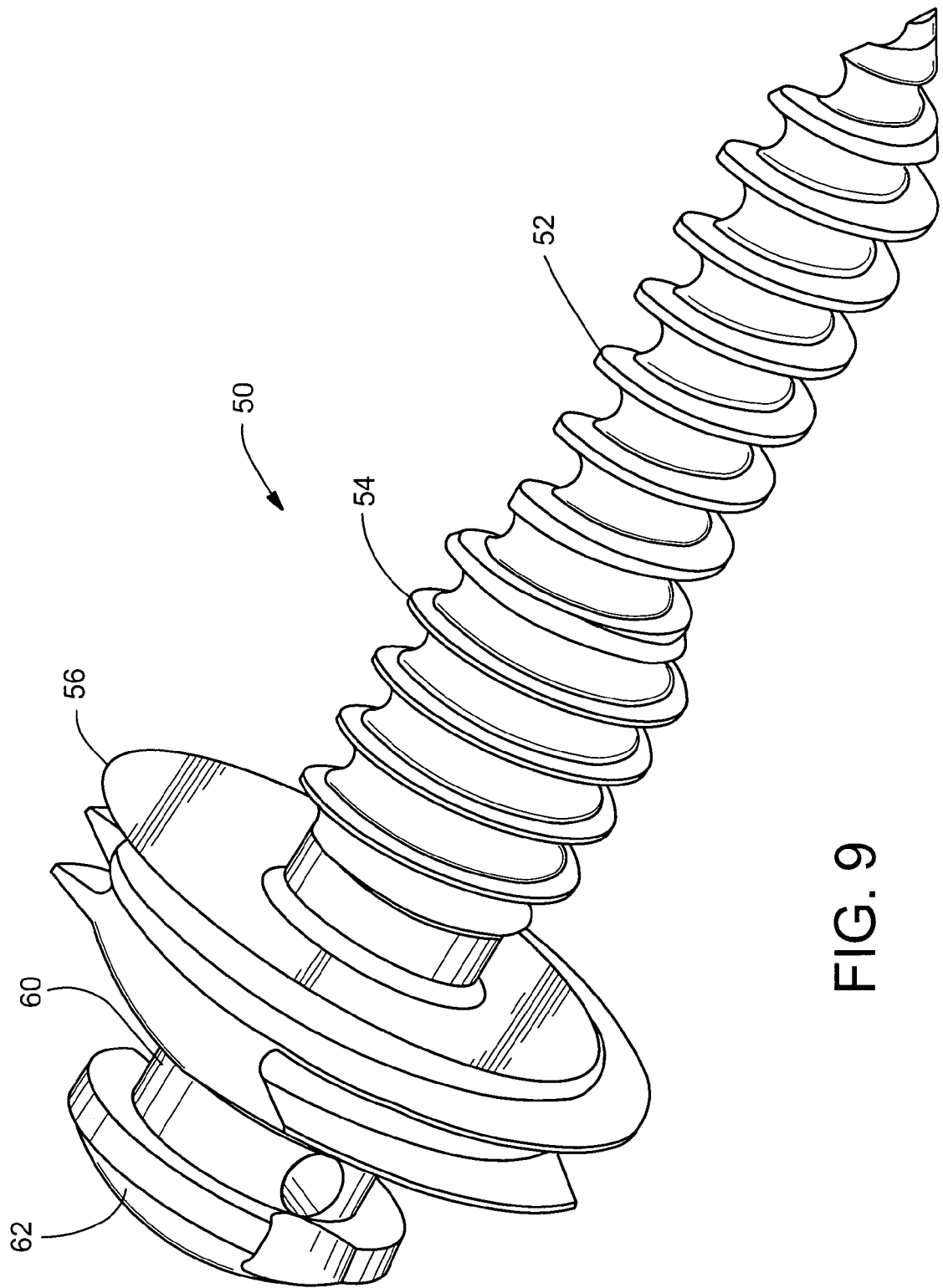
FIG. 9 is a perspective view of the mesial anchor screw shown in FIG. 7.
Figure 10:
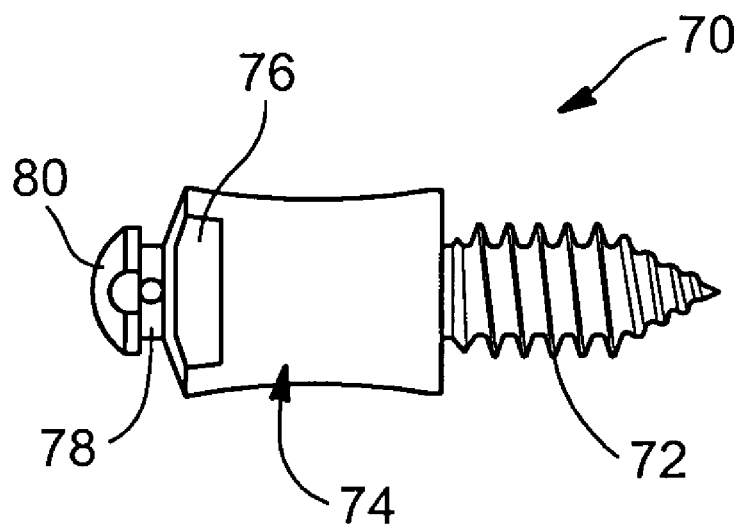
FIG. 10 is a side elevational view of a zygomatic anchor screw of the present invention.

FIGS. 7, 8 and 9 illustrate an anchor screw 50 for placement mesial to either the upper or lower molars. The anchor screw 50 comprises an inner threaded portion 52, a larger intermediate threaded portion 54 and an enlarged threaded washer portion 56 that are similar in construction to the threaded portions 32, 34 and the washer portion 36 of the palatal anchor screw 30 shown in FIGS. 4-6. In the mesial anchor screw 50, the threaded washer portion 56 is of less thickness than the washer portion 36 of the palatal anchor screw 30 for the reason that the gum tissue in the area mesial to the upper or lower molars is of less thickness than that in the palatal area.

The anchor screw 50 comprises an angled nut portion 58, a neck portion 60 and a head portion 62 similar to the nut portion 44, neck portion 40 and head portion 42, respectively, of the palatal anchor screw 30 and thus are not described in detail herein.

As an illustrative example and not by way of limitation, the mesial anchor screw 50 may have a 1.5 mm inner threaded portion 52, a 2.0 mm intermediate threaded portion 54, a thread length of approximately 6.5 mm, and a washer portion 56 of approximately 4 mm outer diameter.

Figure 11:
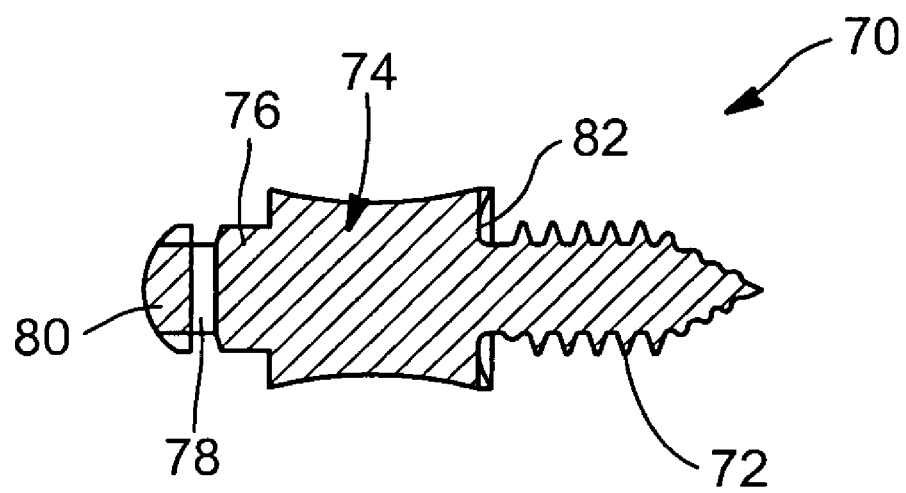
FIG. 11 is a side elevational view in section of the zygomatic anchor screw as shown in FIG. 10.
Figure 12:
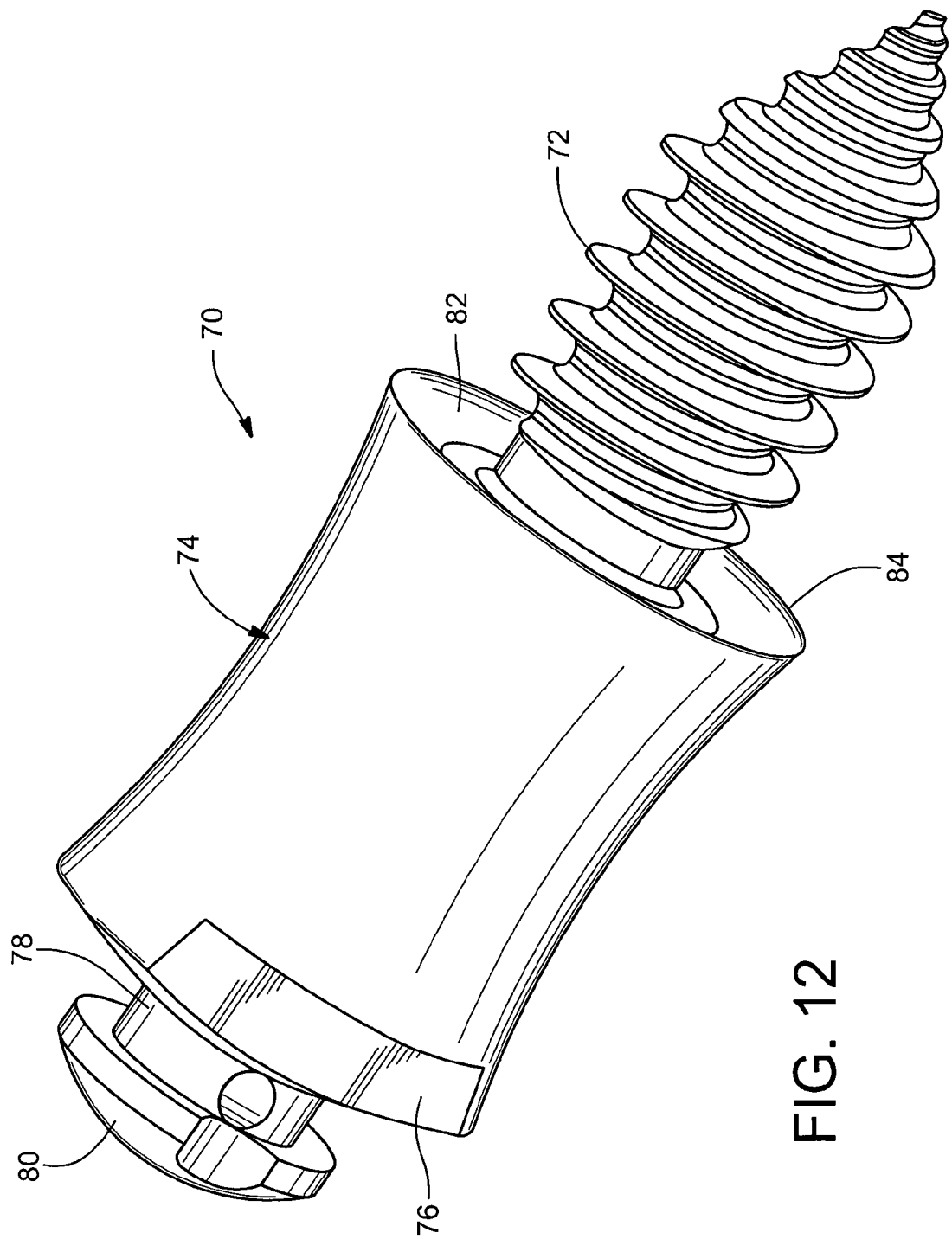
FIG. 12 is a perspective view of the zygomatic anchor screw shown in FIG. 10.
Figure 13:
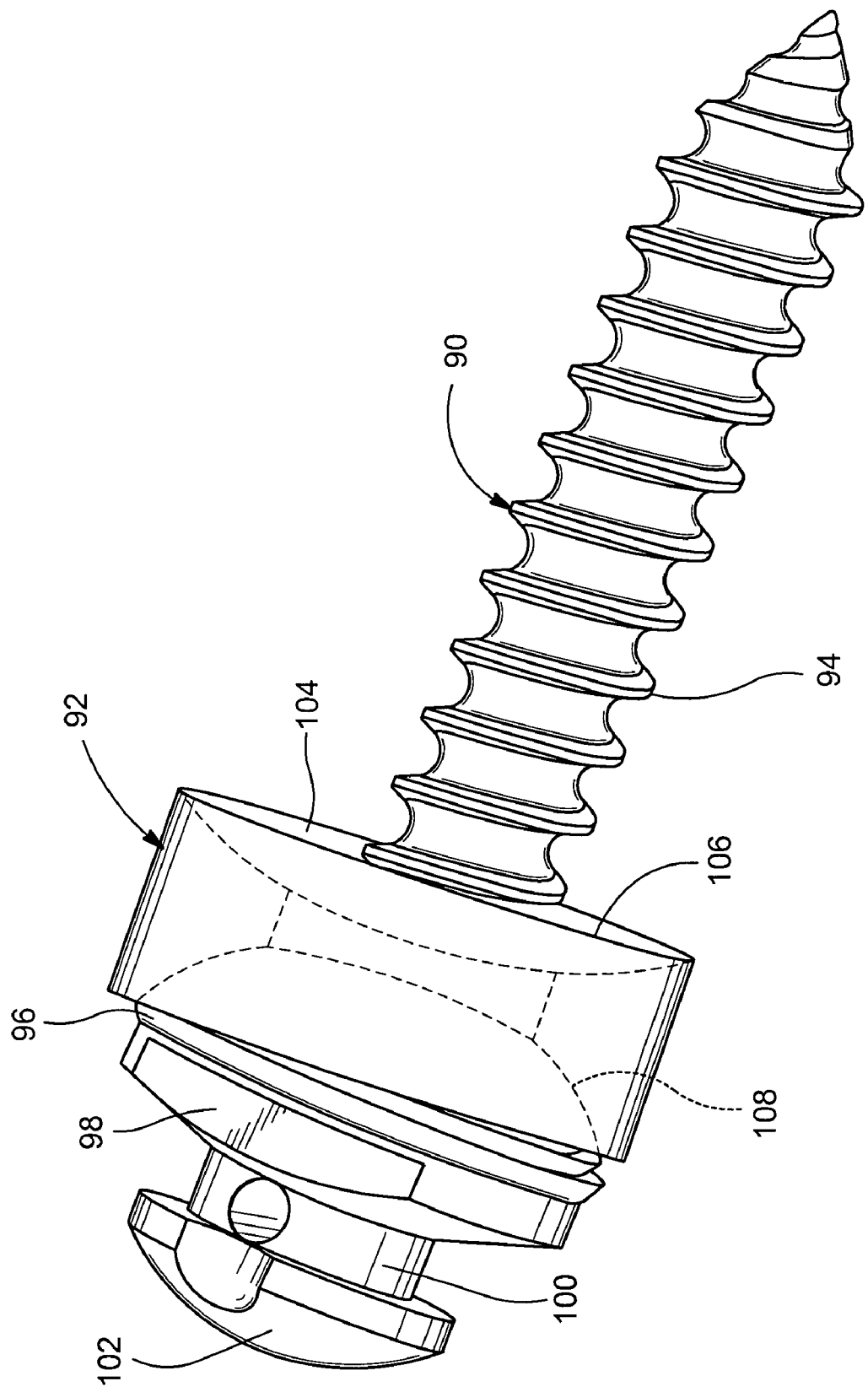
FIG. 13 is a perspective view of a first embodiment of an anchor screw having a flexible and resilient washer in accordance with the present invention.

FIGS. 11-13 illustrate an anchor screw 70 for use in the zygomatic area in the mouth and, more specifically, for placement in the zygomatic process of the maxillary bone. The anchor screw 70 comprises an inner threaded portion 72 that is connected at its outer end with an enlarged and elongated washer portion 74. The outer end of the washer portion 74 merges with an angled nut portion 76 that is connected to a neck portion 78 that is in turn connected to an outer head portion 80. The nut portion 76, neck portion 78 and head portion 80 are similar to the nut portion 14, neck portion 16 and head portion 18 respectively, of the incisal anchor screw 10 and thus are not described in detail herein.

As shown in FIGS. 11 and 12, the inner surface 82 of the washer portion 74 may be concave to provide a sharp outer edge portion 84 that cuts through the gum tissue and engages a cortical bone for lateral support when the threaded portion 72 is installed in the bone in the zygomatic area. The washer portion 74 is elongated and is of a greater length than the washer portion 14 of the incisal anchor screw 10 for the reason that the gum tissue in the zygomatic area is unattached tissue of a greater thickness. In this manner, tissue is prevented from growing over the head portion 80 of the anchor screw 70 to insure that the neck portion 78 and head portion 80 of the anchor screw 70 are fully exposed when the anchor screw 70 is installed in the bone in the zygomatic area.

As an illustrative example and not by way of limitation, the threaded portion 72 of the zygomatic anchor screw 70 may have a starter thread of approximately 2.0 mm and a final thread of approximately 3.0 mm, with a thread length of approximately 5 mm. The inner end of the washer portion 74 may have an outer diameter of approximately 4 mm, and the washer portion 74 may have a thickness of approximately 5 mm. with a concave outer diameter to facilitate the handling and use thereof.

Figure 14:
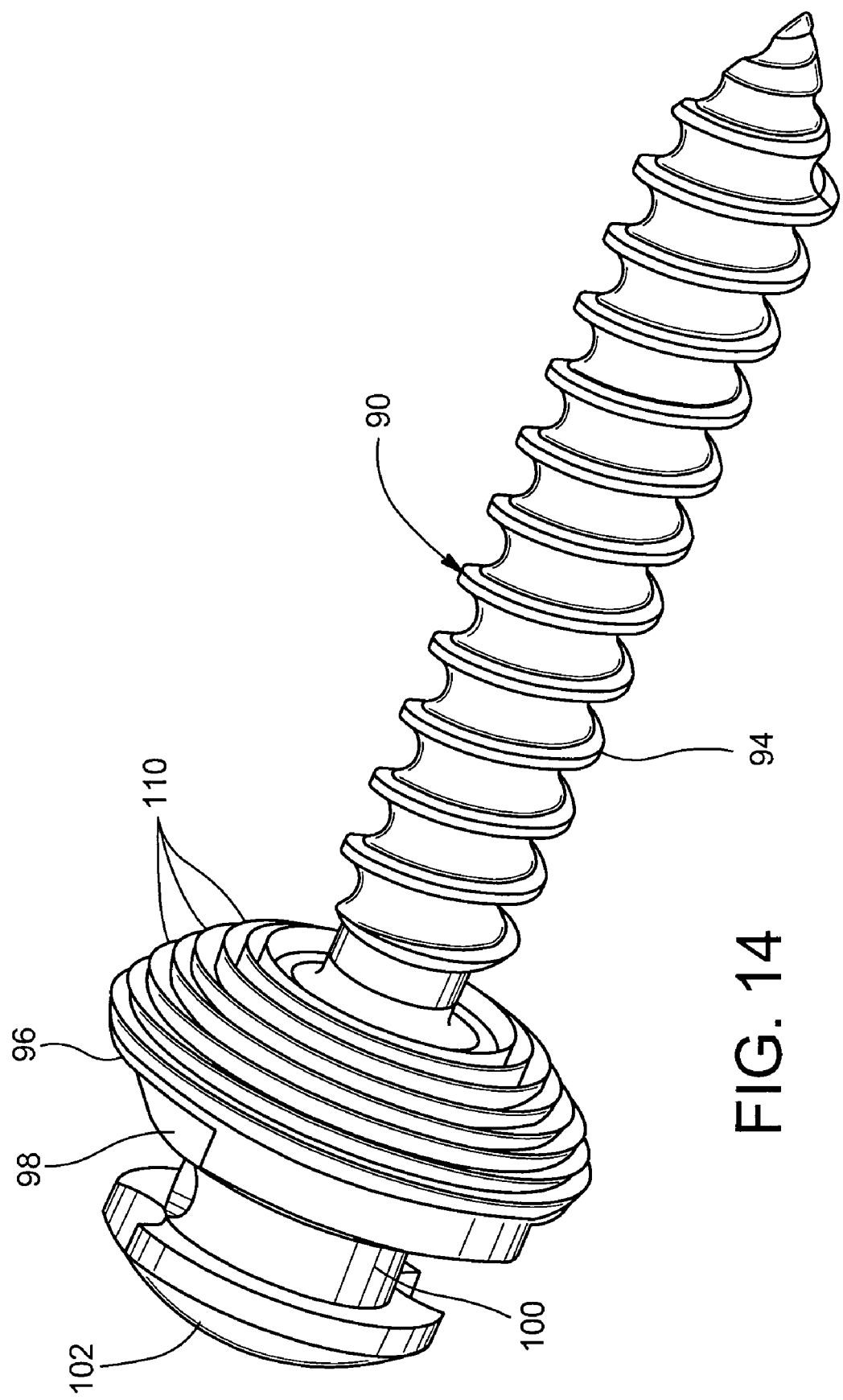
FIG. 14 is a perspective view of the anchor screw shown in FIG. 13 without the washer.

FIGS. 13 and 14 illustrate a further embodiment of the present invention wherein anchor screw 90 of any suitable construction or configuration is provided with a flexible and resilient washer 92 disposed at the outer end of the threaded portion 94 and adjacent to the inner surface of the washer portion 96 of the anchor screw 90. The anchor screw 90 may have an outer angled nut portion 98, a neck portion 100 and a head portion 102 similar to the same components of the anchor screws 10, 30, 50 and 70 disclosed herein.

As shown in FIG. 13, the inner surface 104 of the washer 92 is concave to provide a relatively sharp outer edge 106 for engagement with the outer bone surface when the anchor screw 90 is installed in the bone in a selected area of the mouth. The outer end of the washer 92 is provided with a concave recess 108 of a size and shape complementary to that of the inner end of the washer portion 96 of the anchor screw 90 so that it can be seated therein. As shown in FIG. 14, the inner surface of the washer portion 96 is generally convex and may be formed of a plurality of concentric sharp edge portions 110.

The purpose of the flexible and resilient washer 92 is to engage the outer bone surface for lateral support of the anchor screw 90 when it is installed at various angles to the adjacent bone surface. The sharp concentric portions 110 at the inner end of the washer portion 96 of the anchor screw 90 served to engage the adjacent concave surface 108 of the flexible and resilient washer 92 to hold the washer in place firmly against the outer bone surface for proper lateral support of the anchor screw 90.

Figure 15:
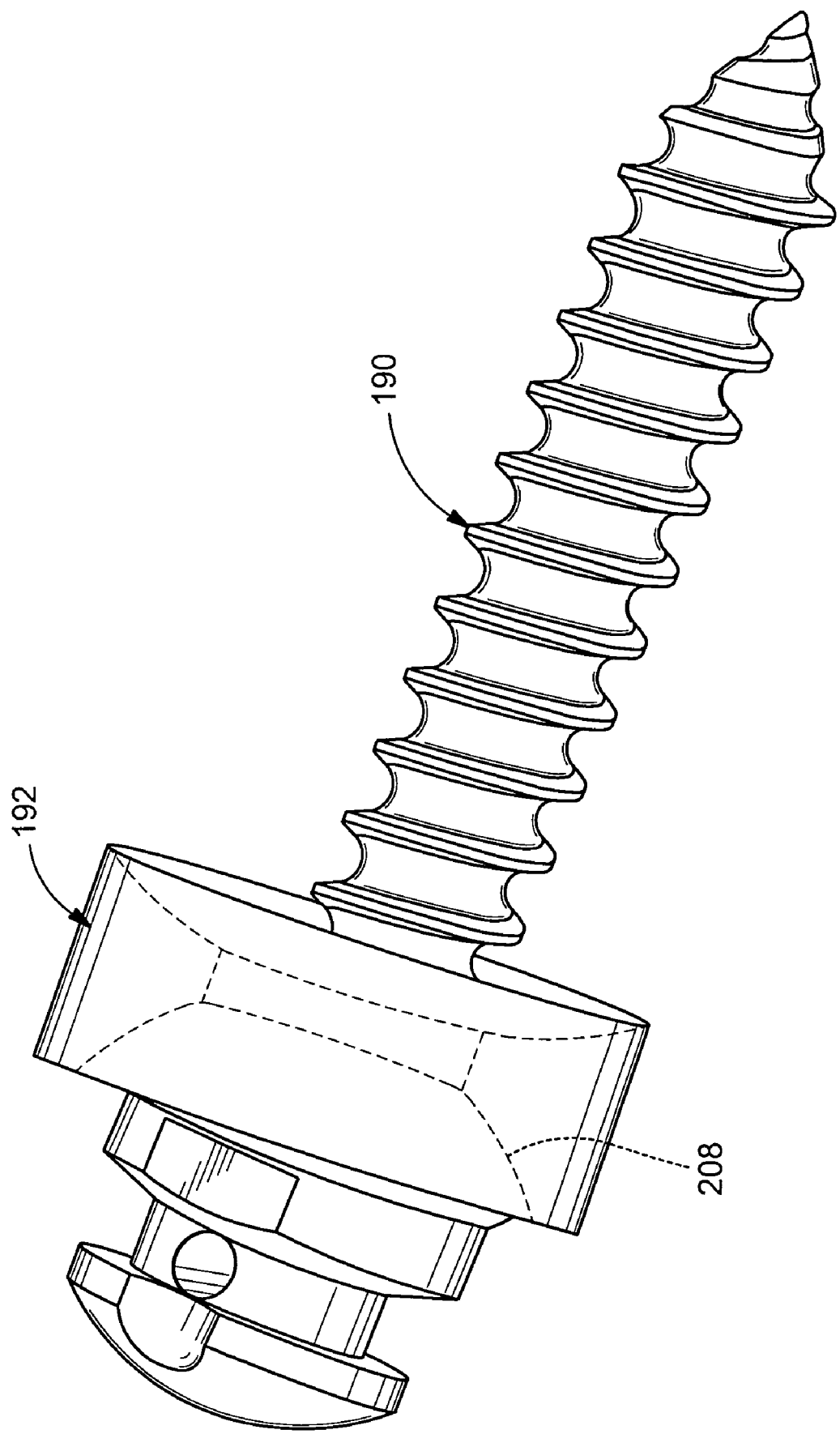
FIG. 15 is a perspective view of a second embodiment of an anchor screw having a flexible and resilient washer.
Figure 16:
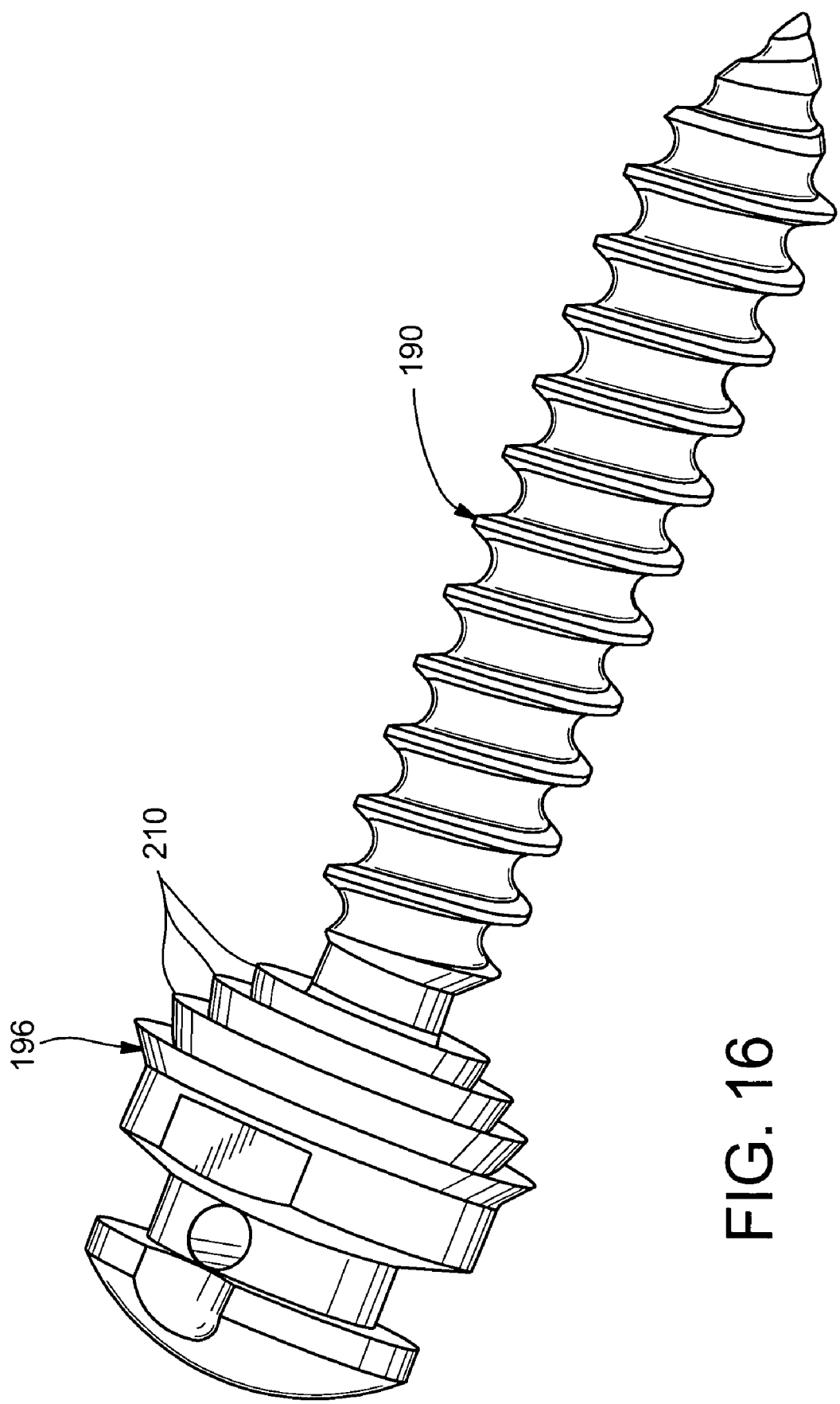
FIG. 16 is a perspective view of the anchor screw shown in FIG. 15 without the washer.

The anchor screw 190 and washer 192 shown in FIGS. 15 and 16 are very similar to the anchor screw 90 and washer 92 shown in FIGS. 13 and 14. As shown in FIG. 16, the anchor screw 190 differs from the anchor screw 90 in that the inner surface of its washer portion 198 is formed of larger concentric sharp edge portions 210 that fit and anchor within the adjacent concave recess 208 in the washer 192.

The washers 92 and 192 may be formed of any suitable flexible and resilient material, such as plastic and, more particularly, ultra high molecular weight polyethylene, Teflon, polyurethane or Peek.

The anchor screws disclosed herein may be formed of any suitable material of sufficient strength and safety for the mouth area, e.g., a metal such as titanium, cobalt chromium or stainless steel.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. Apparatus for anchoring orthodontic appliances in the mouth, comprising anchor screws of different constructions for installation in the bone in different areas of the mouth to insure adequate bone contact and retention, each of the anchor screws having a threaded portion with a longitudinal axis and a washer portion of non-threaded construction at the outer end of the threaded portion, said washer portion being of sufficient width to engage the adjacent exterior bone surface when the threaded portion is installed in the bone to provide lateral support for the threaded portion, wherein said washer portion has a smooth inner surface that is concave and comprises an outer uniform and continuous sharp peripheral edge to facilitate cutting through the adjacent gum tissue and engagement with the underlying adjacent exterior bone surface when the threaded portion is installed in the bone, said peripheral edge lying in a plane that is substantially perpendicular to the longitudinal axis of said threaded portion wherein each of the anchor screws has a neck portion adjacent the outer end of the washer portion, the neck portion having a lateral bore extending therethrough so that a ligature can be extended through the lateral bore to prevent the anchor screw from falling in the mouth.

2. The apparatus of claim 1 wherein each of the anchor screws has an angled nut portion on the outer end of the washer portion for engagement by a tool or driver for rotating and installing the anchor screw in the bone.

3. The apparatus of claim 1 wherein each of the anchor screws has a head portion adjacent the neck portion, the head portion having a pair of lateral recesses that are longitudinally aligned with the opposite ends of the lateral bore to receive therein portions of a ligature extending outwardly from the bore.

4. An anchor screw for anchoring orthodontic appliances in the incisal area of the mouth, said anchor screw comprising an elongated threaded portion having a longitudinal axis and a washer portion of non-threaded construction at the outer end of the threaded portion, said washer portion being of sufficient width to engage the adjacent exterior bone surface when the threaded portion is installed in the bone to provide lateral support for the threaded portion, wherein said washer portion has a smooth inner surface that is concave and comprises an outer uniform and continuous sharp peripheral edge to facilitate cutting through the adjacent gum tissue and engagement with the underlying exterior bone surface when the threaded portion is installed in the bone, said peripheral edge lying in a plane that is substantially perpendicular to the longitudinal axis of said threaded portion wherein said anchor screw has a neck portion adjacent the outer end of the washer portion, the neck portion having a lateral bore extending therethrough so that a ligature can be extended through the lateral bore to prevent the anchor screw from falling in the mouth.

* * * * *